United States Patent [19]

Chang et al.

[11] Patent Number: 5,057,640

[45] Date of Patent: Oct. 15, 1991

[54] PROPYLENE OLIGOMERIZATION OVER SILICA MODIFIED ZEOLITES

[75] Inventors: Clarence D. Chang, Princeton; Paul G. Rodewald, Rocky Hill, both of N.J.

[73] Assignee: Mobil Oil Corp., Fairfax, Va.

[21] Appl. No.: 636,857

[22] Filed: Jan. 2, 1991

[51] Int. Cl.$^5$ .............................................. C07C 2/02
[52] U.S. Cl. ................................................. 585/533
[58] Field of Search ........................................ 585/533

[56] References Cited

U.S. PATENT DOCUMENTS

| | | | |
|---|---|---|---|
| 4,060,568 | 11/1977 | Rodewald | 260/682 |
| 4,145,315 | 3/1979 | Rodewald | 252/455 Z |
| 4,203,869 | 5/1980 | Rollmann | 252/455 Z |
| 4,477,583 | 10/1984 | Rodewald | 502/71 |
| 4,658,079 | 4/1987 | Chen | 585/517 |
| 4,754,096 | 6/1988 | Chang et al. | 585/533 |
| 4,870,038 | 9/1989 | Page et al. | 502/62 |
| 4,876,411 | 10/1989 | Bowes et al. | 585/533 |

*Primary Examiner*—Anthony McFarlane
*Assistant Examiner*—Nhat Phan
*Attorney, Agent, or Firm*—Alexander J. McKillop; Charles J. Speciale; Edward F. Kenehan, Jr.

[57] ABSTRACT

There is provided a process for oligomerizing propylene by contacting propylene with silica modified zeolites. The modification of the zeolite with silica results in a product which is enriched in hydrocarbons falling within the boiling range of jet fuel (330°–480° F.) and diesel fuel (480°–650° F.). The zeolite may be ZSM-5, which may be modified by sorbing methylhydrogensilicone into the pores of the zeolite followed by calcination to convert the sorbed methylhydrogensilicone into amorphous silica.

11 Claims, No Drawings

PROPYLENE OLIGOMERIZATION OVER SILICA MODIFIED ZEOLITES

BACKGROUND

There is provided a process for oligomerizing propylene by contacting propylene with silica modified zeolites. The modification of the zeolite with silica results in a product which is enriched in hydrocarbons falling within the boiling range of jet fuel and diesel fuel.

Propylene oligomerization over acidic catalysts is a known reaction. Over HZSM-5 in a fixed bed, propylene oligomerizes to a nearly Gaussian distribution of products from $C_6$ to $C_{36}$. These products correspond to gasoline, jet fuel, diesel fuel, and a heavy fraction. For the purposes of the present disclosure these fractions are defined in terms of the following boiling ranges:

gasoline = less than 330° F. (166° C.)
jet fuel = 330°–480° F. (166°–249° C.)
diesel fuel = 480°–650° F. (249°–343° C.)
heavy fraction = greater than 650° F. (343° C.)

The heavy fraction is also referred to herein as the 650+° F. fraction or the 650+ F. range product.

Silica modified ZSM-5 can be prepared by impregnation of a silicon containing compound followed by air calcination. U.S. Pat. No. 4,477,583 describes methods for impregnating the exterior surface of zeolites with amorphous silica, whereas U.S. Pat. Nos. 4,145,315; 4,100,219 and 4,060,568 describe methods for impregnating the interior pore space of zeolites with amorphous silica. In accordance with the present invention, it has now been observed that propylene oligomerization over silica modified HZSM-5, modified by this latter technique, gives a product distribution different from that of the parent HZSM-5. The 650+° F. fraction is selectively reduced with a corresponding increase in the lighter fractions. Recycle of the gasoline fraction can give ultimate yields of jet and diesel fuels significantly higher than the corresponding yields using unmodified HZSM-5.

SUMMARY

There is provided a process for oligomerizing propylene, said process comprising contacting propylene with a catalyst under sufficient oligomerization conditions, said catalyst comprising an aluminosilicate zeolite having a silica to alumina molar ratio of at least about 12, a Constraint Index within the approximate range of 1 to 12 and containing interspersed within the interior cystalline structure thereof added amorphous silica in an amount of at least about 0.1 weight percent.

EMBODIMENTS

The present silica-modified catalyst offers a means of selectively producing jet and diesel fuels from inexpensive propylene. Oligomerization to 650+° F. range product is suppressed by the catalyst, and gasoline range product can be recycled to give high ultimate yields of jet and diesel fuels.

The product contains no aromatics which are deleterious to the combustion of jet and diesel fuels. Additionally, the jet fuel product could be extended to include some diesel range material to lower average fuel volatility and increase post crash survivability for airline passengers.

The propylene oligomerization conditions may include a temperature of from about 100° C. to about 400° C., a pressure of from about 0 psig to about 2000 psig, and a weight hourly space velocity of from about 0.1 to about 20. The oligomerization product may comprise less than 25 wt %, e.g., less than 20 wt %, of hydrocarbons having a boiling point of greater than 650° F.

The members of the class of zeolites useful herein have an effective pore size of generally from about 5 to about 8 angstroms, such as to freely sorb normal hexane. In addition, the structures provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolite ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

| Constraint Index (CI) values for some typical materials are: | |
|---|---|
| | CI (at test temperature) |
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index provides a definition of those zeolites which are useful in the instant invention. The very nature of this parameter and the recited technique by which it is determined, however, admit of the possibility that a given zeolite can be tested under somewhat different conditions and thereby exhibit different Constraint Indices. Constrant Index seems to vary somewhat with severity of operations (conversion) and the presence or absences of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C, to about 538° C., the CI will have a value for any given zeolite of interest herein within the approximate range of 1 to 12.

Examples of zeolites having a Constraint Index of from 1 to 12 include ZSM-5, ZSM-11, ZSM-12, ZSM-22, ZSM-23, ZSM-35, ZSM-38 and ZSM-48.

ZSM-5 is described in greater detail in U.S. Pat. Nos. 3,702,886 and Re. 29,948. The entire descriptions contained within those patents particularly the X-ray diffraction pattern of therein disclosed ZSM-5, are incorporated herein by reference.

ZSM-11 is described in greater detail in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. Pat. No. 4,556,477, the entire contents of which is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,406,859. The description of that zeolite, and particularly the specified X-ray diffraction pattern thereof, is incorporated herein by reference.

ZSM-48 is more particularly described in U.S. Pat. No. 4,234,231, the entire contents of which is incorporated herein by reference.

Catalysts useful in the present oligomerization process are described in the aforementioned U.S. Pat. Nos. 4,145,315; 4,100,219 and 4,060,568; the entire contents of which are expressly incorporated herein by reference, especially insofar as these patents describe methods for impregnating the interior pore space of zeolites with amorphous silica. This modification may take place by contacting the crystals of zeolite in a form substantially free of alkali metal, i.e., containing less than about 1.5 weight percent alkali metal and preferably having at least a portion of the original cations associated therewith replaced by ammonium and/or hydrogen, with a silicon-containing compound of molecular dimensions such that it is readily sorbed into the pores of the zeolite. Representative and preferred silicon-containing compounds include silicones of a molecular size capable of entering the pores of the zeolite. The silicone compound utilized is characterized by the general formula:

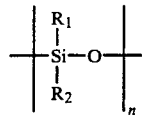

where $R_1$ and $R_2$ are individually selected from the group consisting of hydrogen, methyl, fluorine, chlorine and hydroxy and n is an integer of at least 3 and generally in the range of 4 to 1000. The molecular weight of the silicone compound employed is generally between about 250 and about 60,000 and preferably within the approximate range of 300 to 20,000. Representative silicone compounds include methylhydrogensilicone, dihydrogen silicone, dimethyl silicone, dichlorosilicone, fluorohydrogen silicone and difluorosilicone.

Silicone compounds are preferred as sources of silica in modification of the zeolite catalysts described herein since the zeolites so modified have been found to provide selective conversion of low molecular weight alcohols to light olefins with extremely low production of $C_9 +$ hydrocarbon, e.g., durene. Another silicon-containing compound which may be employed is a silane having the following formula:

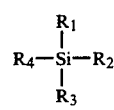

where $R_1$ and $R_2$ are hydrogen, fluorine, chlorine, methyl, ethyl, amino, methoxy or ethoxy; $R_3$ is hydrogen, fluorine, chlorine, methyl, amino or methoxy; and $R_4$ is hydrogen or fluorine. Other suitable silanes include poly-silanes, such as di-silanes, tri-silanes and higher silanes, up to deca-silanes. It is also contemplated to use derivatives of the aforenoted poly-silanes having methyl, chloro or fluoro substituents.

The silicon compound employed may be either in the form of a solution, a liquid or a gas under the conditions of contact with the zeolite. The pores of the latter are preferably, but not necessarily, saturated with the contacting media containing the silicon compound when a silicone compound is employed, it may be dissolved in a suitable solvent therefor, e.g., n-hexane, pentane, heptane, benzene, toluene, xylenes, trimethyl benzene, chloroform, carbon tetrachloride, dichloro benzene or trimethyl benzene. Contact between the silicone compound and the zeolite is maintained at a temperature between about 10° C. and about 200° C. for a period of time sufficient to sorb the ultimately desired amount of silicone therein. Time of contact will generally be within the range of 0.2 to 5 hours, during which time the mixture is desirably subjected to evaporation of the solvent fluid. The resulting residue is then calcined in an oxygen-containing atmosphere, preferably air, at a rate of 0.2° C. to 5° C./minute to a temperature greater than 300° C. but below a temperature at which the crystallinity of the zeolite is adversely affected. Generally, such temperature will be below 700° C. Preferably, the temperature of calcination is within the approximate range of 350° C. to 550° C. The product is maintained at the calcination temperature usually for 1 to 24 hours to yield a zeolite having silica contained in the interior porous structure thereof.

When the employed silicon compound is a silane, the latter desirably undergoes catalyzed hydrolysis, either by base catalyzed hydrolysis, e.g., by contacting the zeolite containing the sorbed silane with a solution of aqueous ammonia or by acid catalyzed hydrolysis in the presence of Lewis or Bronsted acids, such as for example, by contact with an aqueous solution of hydrochloric acid. Contact of the zeolite contained sorbed silane with a suitable acid or base is maintained for a period of time sufficient to effect the desired hydrolysis with evolution of hydrogen. The resulting product is then calcined as above desired to yield a catalyst of the specified crystalline aluminosilicate zeolite having silica contained within its interior structure.

The amount of silica incorporated with the zeolite will depend on several factors. One of these is the time that the zeolite and the silicon-containing source are maintained in contact with each other. With greater contact times, all other factors being equal, a greater amount of silica is incorporated with the zeolite. Other factors upon which the amount of silica incorporated with the zeolite is dependent include temperature, concentration of the treating compound in the contacting media, the degree to which the zeolite has been dried prior to contact with the silicon-containing compound, the conditions of hydrolysis, when practiced, and calcination of the zeolite after contact of the same with the treating compound and the amount and type of binder incorporated with the zeolite. Generally, the amount of silica contained in the interior porous structure of the zeolite will be between about 0.3 and about 40 and preferably between about 0.5 and about 30 weight percent.

The amount of silica incorporated into the zeolite crystal can be assessed from a reduction in the zeolitic sorption capacity. The latter is determined from the amount of n-hexane sorbed at a temperature of 90° C. and a n-hexane partial pressure of 83 mm mercury and is determined from the increase in zeolite weight upon sorption. The decrease in sorption capacity of the zeolite under the above conditions attributable to the presence of added amorphous silica is at least 1 percent and generally in the range of 5 to 60 percent. Representative sorption data for a binder-free zeolite and an alumina-zeolite extrudate are shown below:

| Binder-Free ZSM-5 | Mg. n-hexane Sorbed Per Gram of ZSM-5 |
|---|---|
| No added amorphous silica | 105 |
| Intracrystalline amorphous silica (24%) | 55 |
| Extrudate-65% ZSM-5-35% Al$_2$O$_3$ | |
| No added amorphous silica | 80 |
| Intracrystalline amorphous silica (14%) | 61 |

The oligomerization catalyst can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the layered material can be extruded before drying or partially dried and then extruded.

It may be desired to incorporate the catalyst with another material which is resistant to the temperatures and other conditions employed in the oligomerization process described herein. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with zeolite, i.e., combined therewith or present during its synthesis, which itself is catalytically active may change the conversion and/or selectivity of the catalyst. Inactive materials suitably serve as diluents to control the amount of conversion so that oligomerization products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with catalysts include the montmorillonite and kaolin family, which families include the subbentonites, and the kaolins commonly known as Dixie, McNamee, Georgia and Florida clays or others in which the main mineral constituent is halloysite, kaolinite, dickite, macrite, or anauxite. Such clays can be used in the raw state as originally mined or initially subjected to calcination, acid treatment or chemical modification. Binders useful for compositing with zeolites also include inorganic oxides, notably alumina.

In addition to the foregoing materials, the catalysts can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of finely divided catalyst and inorganic oxide matrix vary widely, with the layered material content ranging from about 1 to 90 percent by weight and more usually, particularly when the composite is prepared in the form of beads, in the range of about 2 to about 80 weight of the composite.

EXAMPLES

In a typical catalyst preparation, 12.00 g HZSM-5 was added to 0.63 g methylhydrogensilicone dissolved in 50 cc hexane. The hexane was distilled off and the residue calcined at 2° C./min to 538° C., then 7 hours at 538° C. The resultant catalyst contained 5% added silica.

Propylene oligomerization was carried out at 200° C. and 600 psig in a fixed bed reactor using 2.00 g catalyst. The propylene weight hourly space velocity was 0.25 or 0.125.

Propylene oligomerization was carried out as above over HZSM-5 and silica modified HZSM-5. The following table compares the results.

| Catalyst | WHSV | Product Distribution, wt % | | | | Ultimate Yield Jet + Diesel |
|---|---|---|---|---|---|---|
| | | 330− Gasoline | 330− 480 Jet Fuel | 480− 650 Diesel Fuel | 650+ Heavy | |
| HZSM-5 | 0.25 | 13 | 25 | 35 | 27 | 69 |
| " | 0.125 | 11 | 17 | 34 | 38 | 57 |
| SiO$_2$-HZSM-5 | 0.25 | 31 | 39 | 24 | 6 | 91 |
| | 0.125 | 27 | 35 | 27 | 11 | 84 |

Relative to HZSM-5, the SiO$_2$-ZSM-5 catalyst produces significantly less 650+° F. range product (6% and 11% vs 27% and for HZSM-5) At approximately the same diesel yield (34% vs 27%), the 650+° F. fraction yield is selectively reduced from 38% to 11% by the silica-modified catalyst. Similarly, for diesel yields of 35% and 24%, the silica-modified catalyst lowers the 650+° F. fraction yield from 27% to only 6%.

As a consequence of the lower 650+° F. fraction yield, increased lighter product is formed. Recycle of the gasoline fraction to extinction gives ultimate yields for the other products. The ultimate yields of jet fuel + diesel fuel are significantly higher for the silica-modified catalyst (91% and vs 69% and 57% for HZSM-5).

What is claimed is:

1. A process for oligomerizing propylene, said process comprising contacting propylene with a catalyst under sufficient oligomerization conditions, said catalyst comprising an aluminosilicate zeolite having a silica to alumina molar ratio of at least about 12, a Constraint Index within the approximate range of 1 to 12 and containing interspersed within the interior cystalline structure thereof added amorphous silica in an amount of at least about 0.1 weight percent based on the weight of the zeolite.

2. A process according to claim 1, wherein the amount of said added amorphous silica is at least 0.3 weight percent based on the weight of the zeolite.

3. A process according to claim 2, wherein the zeolite which is modified with added amorphous silica has an n-hexane sorption capacity at a temperature of 90° C. and an n-hexane partial pressure of 83 mm of mercury which is at least 1 percent less than the corresponding sorption capacity under identical conditions for the unmodified zeolite.

4. A process according to claim 1, wherein the amount of added amorphous silica is between about 0.5 and about 30 weight percent based on the weight of the zeolite.

5. A process according to claim 1, wherein said zeolite is ZSM-5.

6. A process according to claim 1, wherein said added amorphous silica is added to said zeolite by (i) contacting said zeolite with a silicone under conditions such that the silicone is sorbed into the pores of the zeolite and (ii) calcining the zeolite under conditions sufficient the convert the sorbed silicone into amorphous silica.

7. A process according to claim 6, wherein said silicone is methylhydrogensilicone.

8. A process according to claim 1, wherein said oligomerization conditions include a temperature of from about 100° C. to about 400° C., a pressure of from about 0 psig to about 2000 psig, and a weight hourly space velocity of from about 0.1 to about 20.

9. A process according to claim 6, wherein said zeolite is ZSM-5.

10. A process according to claim 1, wherein the oligomerization product comprises less than 25 wt % of hydrocarbons having a boiling point of greater than 650° F.

11. A process according to claim 1, where the oligomerization product comprises less than 20 wt % of hydrocarbons having a boiling point of greater than 650° F.

* * * * *